United States Patent
Kramer et al.

(10) Patent No.: US 6,501,988 B2
(45) Date of Patent: Dec. 31, 2002

(54) APPARATUS AND METHOD FOR VENTRICULAR RATE REGULARIZATION WITH BIVENTRICULAR SENSING

(75) Inventors: Andrew P. Kramer, Stillwater, MN (US); Jeffrey E. Stahmann, Ramsey, MN (US); Julio C. Spinelli, Shoreview, MN (US); Jiang Ding, Maplewood, MN (US)

(73) Assignee: Cardiac Pacemakers Inc., St. Paul, MN (US)

(*) Notice: Subject to any disclaimer, the term of this patent is extended or adjusted under 35 U.S.C. 154(b) by 16 days.

(21) Appl. No.: 09/748,358

(22) Filed: Dec. 26, 2000

(65) Prior Publication Data

US 2002/0082648 A1 Jun. 27, 2002

(51) Int. Cl.[7] .............................................. A61N 1/362
(52) U.S. Cl. ............................................. 607/9; 607/25
(58) Field of Search ....................................... 607/9, 25

(56) References Cited

U.S. PATENT DOCUMENTS

| | | | |
|---|---|---|---|
| 3,857,399 A | 12/1974 | Zacouto | 128/419 P |
| 4,030,510 A | 6/1977 | Bowers | 128/419 |
| 4,059,116 A | 11/1977 | Adams | 128/419 PG |
| 4,163,451 A | 8/1979 | Lesnick et al. | 128/419 PG |
| 4,556,063 A | 12/1985 | Thompson et al. | 128/419 PT |
| 4,830,006 A | 5/1989 | Haluska et al. | 607/4 |
| 4,905,697 A | 3/1990 | Heggs et al. | 128/419 PG |
| 4,917,115 A | 4/1990 | Flammang et al. | 128/419 PG |
| 4,920,965 A | 5/1990 | Funke et al. | 128/419 PG |
| 4,928,688 A | 5/1990 | Mower | 128/419 PG |
| 4,945,909 A | 8/1990 | Fearnot et al. | 128/419 PG |
| 4,998,974 A | 3/1991 | Aker | 128/419 PG |
| 5,085,215 A | 2/1992 | Nappholz et al. | 128/419 PG |
| 5,101,824 A | 4/1992 | Lekholm | 128/419 PG |
| 5,127,404 A | 7/1992 | Wyborny et al. | 128/419 P |

(List continued on next page.)

FOREIGN PATENT DOCUMENTS

| | | | |
|---|---|---|---|
| EP | 0033418 | 12/1980 | A61N/1/36 |
| WO | 93/02746 | 2/1993 | A61N/1/368 |
| WO | 97/11745 | 4/1997 | A61N/1/362 |
| WO | 98/48891 | 11/1998 | A61N/1/362 |

OTHER PUBLICATIONS

*Harmony, Automatic Dual Chamber Pacemaker, Product Information and Programming Guide*, Viatron Medical, Harmony Dual Chamber mentioned in publication Clinica, 467, p. 16, (Sep. 11, 1991), "Rate Devices Impact Pacemaker Market", and Clinica, 417, p. 9, (Sep. 5, 1990), "French CNH Equipment Approvals"., 22 p.

(List continued on next page.)

*Primary Examiner*—Carl Layno
(74) *Attorney, Agent, or Firm*—Schwegman, Lundberg, Woessner & Kluth P.A.

(57) ABSTRACT

A method and system for operating a cardiac pacemaker which employs pacing therapy to regularize the ventricular rhythm together with biventricular sensing. Biventricular sensing allows the ventricular rate regularization to be accomplished with greater hemodynamic stability.

26 Claims, 2 Drawing Sheets

U.S. PATENT DOCUMENTS

| | | | | |
|---|---|---|---|---|
| 5,129,394 | A | 7/1992 | Mehra | 128/419 PG |
| 5,139,020 | A | 8/1992 | Koestner et al. | 128/419 PG |
| 5,156,154 | A | 10/1992 | Valenta, Jr. et al. | 128/661.09 |
| 5,183,040 | A | 2/1993 | Nappholz et al. | 128/419 PG |
| 5,188,106 | A | 2/1993 | Nappholz et al. | 128/419 PG |
| 5,207,219 | A | 5/1993 | Adams et al. | 128/419 D |
| 5,282,836 | A | 2/1994 | Kreyenhagen et al. | 607/4 |
| 5,284,491 | A | 2/1994 | Sutton et al. | 607/17 |
| 5,292,339 | A | 3/1994 | Stephens et al. | 607/15 |
| 5,312,452 | A | 5/1994 | Salo | 607/17 |
| 5,331,996 | A | 7/1994 | Bennett et al. | 128/696 |
| 5,334,220 | A | 8/1994 | Sholder | 607/9 |
| 5,350,409 | A | 9/1994 | Stoop et al. | 607/17 |
| 5,365,932 | A | 11/1994 | Greenhut | 128/696 |
| 5,383,910 | A | 1/1995 | den Dulk | 607/14 |
| 5,391,189 | A | 2/1995 | van Krieken et al. | 607/17 |
| 5,395,397 | A | 3/1995 | Lindgren et al. | 607/9 |
| 5,400,796 | A | 3/1995 | Wecke | 128/705 |
| 5,411,524 | A | 5/1995 | Rahul | 607/4 |
| 5,411,531 | A | 5/1995 | Hill et al. | 607/14 |
| 5,417,714 | A | 5/1995 | Levine et al. | 607/9 |
| 5,423,869 | A | 6/1995 | Poore et al. | 607/18 |
| 5,462,060 | A | 10/1995 | Jacobson et al. | 128/702 |
| 5,480,413 | A | 1/1996 | Greenhut et al. | 607/14 |
| 5,486,198 | A | 1/1996 | Ayers et al. | 607/5 |
| 5,487,752 | A | 1/1996 | Salo et al. | 607/17 |
| 5,507,782 | A | 4/1996 | Kieval et al. | 607/9 |
| 5,507,784 | A | 4/1996 | Hill et al. | 607/14 |
| 5,514,163 | A | 5/1996 | Markowitz et al. | 607/9 |
| 5,522,859 | A | 6/1996 | Stroebel et al. | 607/19 |
| 5,527,347 | A | 6/1996 | Shelton et al. | 607/9 |
| 5,534,016 | A | 7/1996 | Boute | 607/9 |
| 5,540,727 | A | 7/1996 | Tockman et al. | 607/18 |
| 5,545,186 | A | 8/1996 | Olson et al. | 607/14 |
| 5,560,369 | A | 10/1996 | McClure et al. | 128/704 |
| 5,584,864 | A | 12/1996 | White | 607/5 |
| 5,584,867 | A | 12/1996 | Limousin et al. | 607/9 |
| 5,626,620 | A | 5/1997 | Kieval et al. | 607/9 |
| 5,626,622 | A | 5/1997 | Cooper | 607/18 |
| 5,626,623 | A | 5/1997 | Kieval et al. | 607/23 |
| 5,632,267 | A | 5/1997 | Hognelid et al. | 607/5 |
| 5,674,255 | A | 10/1997 | Walmsley et al. | 607/14 |
| 5,690,689 | A | 11/1997 | Sholder | 607/24 |
| 5,700,283 | A | 12/1997 | Salo | 607/17 |
| 5,713,929 | A | 2/1998 | Hess et al. | 607/14 |
| 5,713,932 | A | 2/1998 | Gillberg et al. | 607/27 |
| 5,716,383 | A | 2/1998 | Kieval et al. | 607/9 |
| 5,725,561 | A | 3/1998 | Stroebel et al. | 607/9 |
| 5,730,141 | A | 3/1998 | Fain et al. | 128/705 |
| 5,730,142 | A | 3/1998 | Sun et al. | 128/705 |
| 5,738,096 | A | 4/1998 | Ben-Haim | 128/653.1 |
| 5,741,308 | A | 4/1998 | Sholder | 607/9 |
| 5,749,906 | A | 5/1998 | Kieval et al. | 607/9 |
| 5,755,736 | A | 5/1998 | Gillberg et al. | 607/4 |
| 5,755,737 | A | 5/1998 | Prieve et al. | 607/4 |
| 5,755,740 | A | 5/1998 | Nappholz | 607/18 |
| 5,776,164 | A | 7/1998 | Ripart | 607/5 |
| 5,776,167 | A | 7/1998 | Levine et al. | 607/9 |
| 5,788,717 | A | 8/1998 | Mann et al. | 607/14 |
| 5,792,193 | A | 8/1998 | Stoop | 607/14 |
| 5,800,464 | A | 9/1998 | Kieval | 607/9 |
| 5,800,471 | A | 9/1998 | Baumann | 607/25 |
| 5,814,077 | A | 9/1998 | Sholder et al. | 607/9 |
| 5,814,085 | A | 9/1998 | Hill | 607/14 |
| 5,836,975 | A | 11/1998 | DeGroot | 607/5 |
| 5,836,987 | A | 11/1998 | Baumann et al. | 607/17 |
| 5,846,263 | A | 12/1998 | Peterson et al. | 607/14 |
| 5,855,593 | A | 1/1999 | Olson et al. | 607/9 |
| 5,861,007 | A | 1/1999 | Hess et al. | 607/9 |
| 5,873,895 | A | 2/1999 | Sholder et al. | 607/9 |
| 5,873,897 | A | 2/1999 | Armstrong et al. | 607/14 |
| 5,893,882 | A | 4/1999 | Peterson et al. | 607/14 |
| 5,897,575 | A | 4/1999 | Wickham | 607/4 |
| 5,902,324 | A | * 5/1999 | Thompson et al. | 607/9 |
| 5,928,271 | A | 7/1999 | Hess et al. | 607/14 |
| 5,931,857 | A | 8/1999 | Prieve et al. | 607/14 |
| 5,935,081 | A | 8/1999 | Kadhiresan | 600/513 |
| 5,941,471 | A | 8/1999 | Murayama et al. | 242/261 |
| 5,944,744 | A | 8/1999 | Paul et al. | 607/9 |
| 5,951,592 | A | 9/1999 | Murphy | 607/4 |
| 5,978,707 | A | 11/1999 | Krig et al. | 607/14 |
| 5,978,710 | A | 11/1999 | Prutchi et al. | 607/17 |
| 5,983,138 | A | 11/1999 | Kramer | 607/9 |
| 5,987,356 | A | 11/1999 | DeGroot | 607/5 |
| 5,991,656 | A | 11/1999 | Olson et al. | 607/4 |
| 5,999,850 | A | 12/1999 | Dawson et al. | 607/4 |
| 6,026,320 | A | 2/2000 | Carlson et al. | 600/510 |
| 6,044,298 | A | 3/2000 | Salo et al. | 607/17 |
| 6,049,735 | A | 4/2000 | Hartley et al. | 607/9 |
| 6,052,620 | A | 4/2000 | Gillberg et al. | 607/4 |
| 6,081,745 | A | 6/2000 | Mehra | 607/4 |
| 6,263,242 | B1 | * 7/2001 | Mika et al. | 607/9 |
| 6,285,907 | B1 | * 9/2001 | Kramer et al. | 607/9 |

OTHER PUBLICATIONS

*Metrix Model 3020 Implantable Atrial Defibrillator*, Physician's Manual, InControl, Inc., Redmond, WA, pp. 4–24—4–27, (1998).

Ayers, G.M., et al., "Ventricular Proarrhythmic Effects of Ventricular Cycle Length and Shock Strength in a Sheep Model of Transvenous Atrial Defibrillation", *Circulation*, 89 (1), pp. 413–422, (Jan. 1994).

Duckers, H.J., et al., "Effective use of a novel rate–smoothing algorithm in atrial fibrillation by ventricular pacing", *European Heart Journal*, 18, pp. 1951–1955, (1997).

Fahy, G.J., et al., "Pacing Strategies to Prevent Atrial Fibrillation", *Atrial Fibrillation*, 14 (4), pp. 591–596, (Nov. 1996).

Greenhut, S., et al., "Effectiveness of a Ventricular Rate Stabilization Algorithm During Atrial Fibrillation in Dogs", *Pace Abstract*, Abstract No. 60, 1 p., (1996).

Heuer, H., et al., "Dynamic Dual–Chamber Overdrive Pacing with an Implantable Pacemaker System: A New Method for Terminating Slow Ventricular Tachycardia", *Zeitschrift fur Kardiologie*, 75, German Translation by the Ralph McElroy Translation Company, Austin, TX, 5 p., (1986).

Mehra, R., et al., "Prevention of Atrial Fibrillation/Flutter by Pacing Techniques", *Interventional Electrophysiology, Second Edition*, Chapter 34, Futura Publishing Company, Inc., pp. 521–540, (1996).

Wittkampf, F., et al., "Rate Stabilization by Right Ventricular Pacing in Patients with Atrial Fibrillation", *Pace*, 9, pp. 1147–1153, (1986).

* cited by examiner

APPARATUS AND METHOD FOR VENTRICULAR RATE REGULARIZATION WITH BIVENTRICULAR SENSING

CROSS REFERENCE TO RELATED APPLICATIONS

This application is related to the following co-pending, commonly assigned patent application: "System Providing Ventricular Pacing and Biventricular Coordination," U.S. Ser. No. 09/316,588, the disclosure of which is herein incorporated by reference in its entirety.

FIELD OF THE INVENTION

This invention pertains to cardiac pacemakers and methods for operating such devices. In particular, the invention relates to methods for employing pacing therapy to maintain hemodynamic stability.

BACKGROUND

Ventricular tachyarrhythmias, in which the ventricles beat more rapidly and irregularly than normal, can be due to a variety of etiologies. One common cause, for example, is atrial fibrillation where the atria depolarize in a chaotic fashion with no effective pumping action. The intrinsic ventricular rhythm that occurs during an episode of atrial fibrillation is a result of the chaotically occurring depolarizations occurring in the atria being passed through the AV node to the ventricles. The intrinsic ventricular rate is thus governed by the cycle length of the atrial fibrillation and the refractory period of the AV node. Although the intrinsic ventricular rate is less than the atrial rate, due to the refractory period of the AV node, it is still rapid and irregular. When the ventricles contract at irregular intervals, the contraction can occur prematurely before diastolic filling is complete which decreases the stroke volume for that contraction. This can be especially significant in, for example, congestive heart failure patients who are already hemodynamically compromised. Concomitant atrial fibrillation where the atria no longer act as effective priming pumps can also contribute to the problem. An irregular ventricular rate can thus depress cardiac output and cause such symptoms as dyspnea, fatigue, vertigo, and angina. An objective of the present invention is to use pacing therapy to maintain hemodynamic stability in the presence of an irregular intrinsic ventricular rhythm.

SUMMARY OF THE INVENTION

The present invention is a system and method for regularizing the ventricular rate by adjusting the lower rate limit of a pacemaker in accordance with changes in the measured intrinsic ventricular rate. By making the ventricular escape interval track a mean interval between intrinsic beats, less variability in the overall ventricular rhythm is allowed by the pacemaker. Because the ventricular rate regularization keeps the ventricular escape interval close to the interval between intrinsic beats, however, the risk of delivering a pace coincident with an intrinsic depolarization is increased. Such a pace produces a fusion beat which is hemodynamically inefficient and tends to counteract the beneficial effects of ventricular rate regularization in maintaining hemodynamic stability. In accordance with the invention, the risk of producing fusion beats is reduced by providing a ventricular sensing channel for each ventricle and inhibiting ventricular pacing when a ventricular depolarization is detected from either ventricle before the expiration of the ventricular escape interval. Such biventricular sensing is employed whether the pacemaker is operating in a univentricular or biventricular pacing mode.

DETAILED DESCRIPTION OF THE INVENTION

Figure 1:
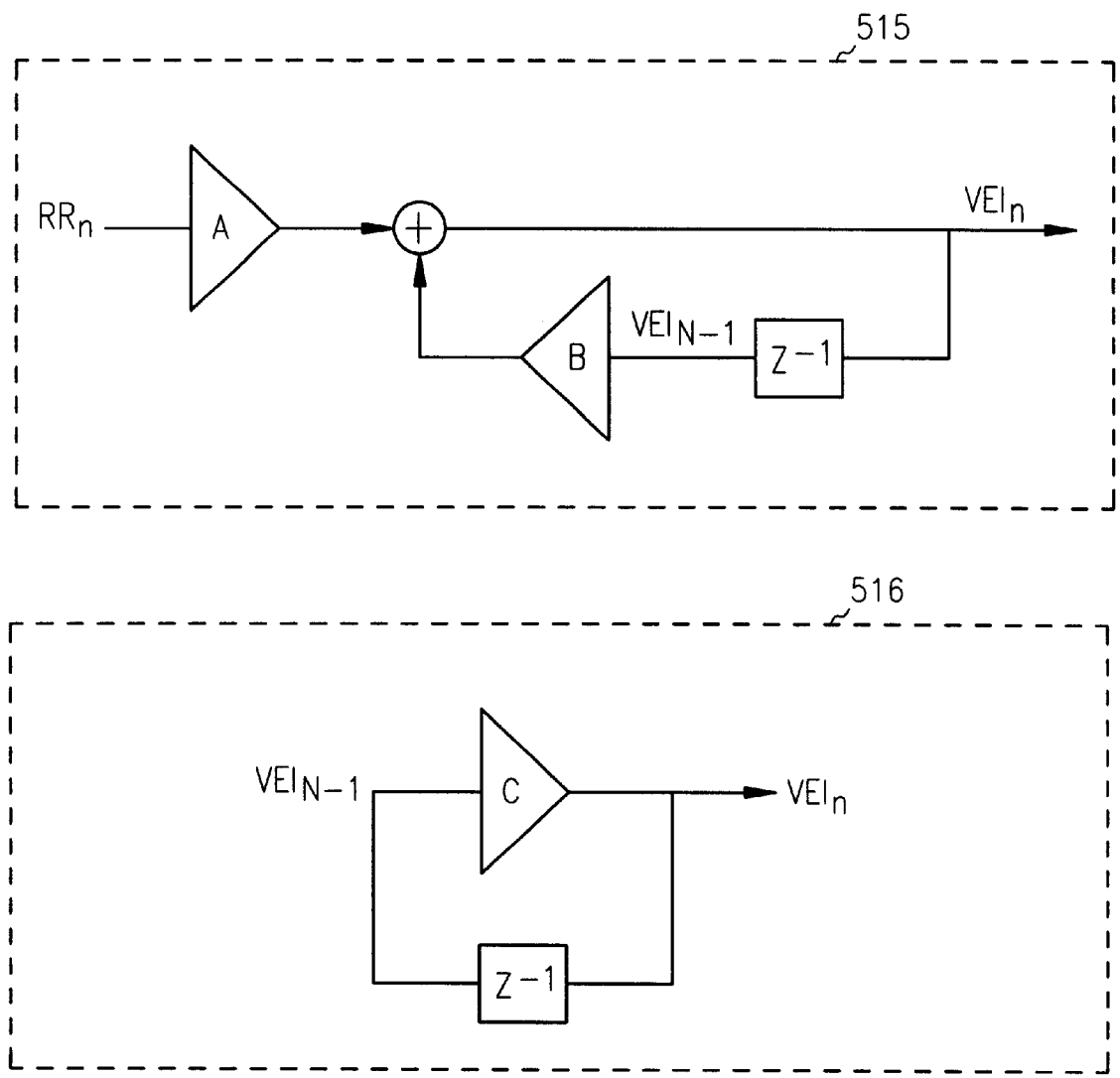
FIG. 1 shows an exemplary filter implementation of a ventricular rate regularization system.

Cardiac pacemakers are cardiac rhythm management devices that provide electrical stimulation in the fonn of pacing pulses to selected chambers of the heart (i.e., the atrium and/or ventricle). As the term is used herein, pacing includes not only electrical stimulation delivered to the heart in order to enforce a particular rate, but also electrical stimulation delivered in order to synchronize the electromechanical activation of the heart and improve pumping function. Furthermore, a pacemaker should be regarded as any cardiac rhythm management device that performs cardiac pacing, including implantable cardioverter/defibrillators having a pacing functionality. Pacemakers typically have a programmable electronic controller that causes the pacing pulses to be output in response to lapsed time intervals and sensed electrical activity (i.e., intrinsic heart beats not a result of a pacing pulse). Implantable pacemakers sense intrinsic cardiac electrical activity by means of electrodes disposed near or within the chamber to be sensed. A depolarization wave associated with an intrinsic contraction of the atria or ventricles that is detected by the pacemaker is referred to as an atrial sense or ventricular sense, respectively. A pacing pulse delivered to a heart chamber, either an atrial pace or a ventricular pace, causes a contraction in the absence of an intrinsic beat.

A pacing mode is defined by which chambers are paced and which events trigger or inhibit pacing. Most pacemakers are programmed to perform bradycardia pacing in a so-called demand mode (a.k.a., synchronous mode), where a pacing pulse is delivered to a heart chamber during a cardiac cycle only when no intrinsic beat by the chamber is detected. An escape interval is defined for each paced chamber, which is the maximum time interval in which a beat must be detected before a pace will be delivered. For example, in a ventricular demand pacing mode, the ventricular escape interval begins with either a ventricular pace or sense. If the ventricular escape interval expires without a subsequent ventricular sense, a ventricular pace is delivered. The reciprocal of the ventricular escape interval is the LRL or lower rate limit which defines the minimum rate at which the ventricles will be paced in a ventricular pacing mode in the absence of spontaneous activity.

Ventricular rate regularization (VRR) is a ventricular pacing mode in which the LRL of the pacemaker is dynamically adjusted in accordance with a detected intrinsic ventricular rate. When a pacemaker is operating in a ventricular demand pacing mode (e.g., VVI), intrinsic ventricular beats occur when the instantaneous intrinsic rate rises above the LRL of the pacemaker. Thus, paces can be interspersed with intrinsic beats, and the overall ventricular rhythm as a result of both paces and intrinsic beats is determined by the LRL and the mean value and variability of the intrinsic ventricular rate. VRR regularizes the overall ventricular rhythm by adjusting the LRL of the pacemaker in accordance with changes in the measured intrinsic rate.

The intrinsic ventricular rate is the rate at which intrinsic ventricular beats occur and can be defined both instantaneously and as being at some mean value with a certain variability about that mean. The instantaneous intrinsic rate can be determined by measuring an R-R interval, where an R-R interval is the time between a present ventricular sense (i.e., an R-wave or intrinsic ventricular depolarization) and the preceding ventricular sense or ventricular pace, with the instantaneous rate being the reciprocal of the measured interval. The mean intrinsic rate can be determined by averaging the instantaneous R-R intervals over a period of time. The LRL of a pacemaker is initially set to a programmed base value and defines the ventricular escape interval, which is the maximum time between ventricular beats allowed by the pacemaker and is the reciprocal of the LRL. At any particular mean intrinsic rate above the LRL, a ventricular pace is delivered only when, due to the variability in the intrinsic rate, an R-R interval would be longer than the ventricular escape interval were it allowed to occur. As the mean intrinsic ventricular rate increases above the LRL, fewer paces are delivered and more variability in the overall ventricular rhythm is allowed. The VRR pacing mode counteracts this by increasing the LRL as the mean intrinsic ventricular rate increases to thereby increase the frequency of paced beats which decreases the incidence of long intrinsic R-R intervals and thus lessens the variability in the overall ventricular rate. The VRR mode then decreases the LRL toward its base value as the number of paces delivered increases due to a decrease in either the mean intrinsic ventricular rate or its variability. The LRL adjusted in this manner is also referred to herein as the VRRindicated rate.

In one embodiment of VRR, the LRL is adjusted to increase toward a programmed maximum value by measuring an R-R interval when a ventricular sense occurs and then computing an updated ventricular escape interval based upon the measured R-R interval. When a ventricular pace is delivered, on the other hand, the LRL is made to decay toward the programmed base value. FIG. 1 shows an exemplary implementation of a VRR system made up of a pair of filters 515 and 516 which may be implemented as software executed by the controller 10 and/or with discrete components. Filter 515 is employed to compute the updated ventricular escape interval when a ventricular sense occurs, and filter 516 is used when a ventricular pace is delivered.

When a ventricular sense occurs, the measured R-R interval is input to a recursive digital filter 515 whose output is the updated ventricular escape interval. The filter 515 multiplies the measured R-R interval by a filter coefficient A and then adds the result to the previous value of the output (i.e., the present ventricular escape interval) multiplied by a filter coefficient B. The operation of the filter is thus described by $VEI_n = A(RR_n) + B(VEI_{n-1})$, where A and B are selected coefficients, $RR_n$ is the most recent R-R interval duration, and $VEI_{n-1}$ is the previous value of the ventricular escape interval. A useful way to conceptualize the filter 515 is to decompose the coefficients A and B into a scaling factor $\alpha$ and a weighting coefficient w such that $A = a \cdot w$ and $B = (1-w)$, where w is between 0 and 1. Viewed this way, the filter is seen as computing a weighted average of the present R-R interval multiplied by the scaling factor $\alpha$ and the present ventricular escape interval. The filter thus causes the value of the ventricular escape interval to move toward the present R-R interval multiplied by the scaling factor at a rate determined by the weighting coefficient. This corresponds to the filter moving the pacemaker's LRL toward a fraction $1/\alpha$ of the instantaneous intrinsic ventricular rate, up to a maximum pacing rate MPR, as determined by the measured R-R interval. If a ventricular sense has occurred, the current LRL is necessarily less than the measured instantaneous intrinsic ventricular rate. If it is also less than $1/\alpha$ of the intrinsic rate, the LRL is increased by the filter up to a value that is $1/\alpha$ of the intrinsic rate (as limited by the MPR) to result in more pacing and less variability in the overall ventricular rhythm.

When a ventricular pace is delivered due to expiration of the ventricular escape interval without a ventricular sense, filter 516 multiplies the present ventricular escape interval by a filter coefficient C so that $VEI_n = C(VEI_{n-1})$. To provide stable operation, the coefficient C must be set to a value greater than 1. Filter 516 then causes the ventricular escape interval to increase in an exponential manner with each pace as successive values of the escape interval are input to the filter up to a value corresponding to the base LRL.

The updating of the ventricular escape interval may be performed in various ways including on a beat-to-beat basis, at periodic intervals, or with averages of successive R-R intervals. In a presently preferred embodiment, however, the updating is performed on a beat-to-beat basis with each ventricular sense or pace causing adjustment of the LRL by filter 515 or 516, respectively. The two filters operating together thus cause the LRL to move closer to $1/\alpha$ of the measured intrinsic rate (up to the MPR) after a ventricular sense and to decay toward the base LRL value after a ventricular pace.

The coefficients a and w (or A and B) and C are selected by the user and may be made programmable so that the behavior of the system can be adjusted to produce the clinically best result in an individual patient. For example, as the scaling factor $\alpha$ is made greater than 1, the filter 515 causes the LRL to move toward a smaller fraction $1/\alpha$ of the detected intrinsic rate which allows more intrinsic beats to occur and greater variability in the overall rhythm. As $\alpha$ is decreased back toward 1, the filter 515 tends to move the LRL of the pacemaker toward a larger fraction of the detected instantaneous intrinsic rate, thus increasing the amount of pacing and decreasing the amount of variability allowed in the overall ventricular rhythm. If $\alpha$ is made smaller than 1, the LRL is moved toward a rate higher than the intrinsic rate, further increasing the amount of pacing to a point where most of the ventricular rhythm is made up of paced beats. The larger the weighting factor w, the faster the LRL is moved to the specified fraction of the intrinsic rate, making the system more responsive to increases in the variability of the intrinsic rhythm. The larger the decay coefficient C, the more rapidly will filter 516 cause the LRL to decrease toward its programmed base value when ventricular paces are delivered due to no ventricular senses being detected within the ventricular escape interval. The controller limits the updated ventricular escape interval as a result of the operations of filters 515 and 516 to minimum and maximum values in accordance with the programmed maximum pacing rate MPR and base lower rate limit LRL, respectively.

As noted, the coefficients of filters 515 and 516 can be made programmable by the user, such as by using a remote programmer. In another embodiment, the user selects a desired performance parameter (e.g., desired degree of rate regularization, desired amount of pacing, desired decay rate, etc.) from a corresponding range of possible values. The appropriate combinations of coefficients for filters 515 and 516 are then automatically selected to provide filter settings that correspond to the selected user-programmed performance parameter. The filter coefficients can also be made functions of other parameters, such as the measured R-R interval and current LRL setting, and dynamically adjusted.

The VRR system in this embodiment uses the programmed base LRL of the pacemaker as the lower limit to which the LRL is permitted to decay when no ventricular senses are detected. The base LRL can be changed periodically by the user with an external programmer, and certain pacemakers also have the capability of dynamically adjusting the LRL in order to adapt to exercise. In such rate-adaptive pacemakers, the LRL is adjusted in accordance with exertion level measurements such as from an accelerometer or minute ventilation sensor in order for the heart rate to more nearly match metabolic demand. The adjusted LRL is then termed the sensor-indicated rate. If a rate-adaptive pacemaker is operated in a VRR mode, the sensor-indicated rate can simply be regarded by the pacemaker as the base LRL. The lower limit for the VRR-indicated rate is then the sensor-indicated rate rather than the programmed base LRL.

As described above, ventricular rate regularization involves adjusting the ventricular escape interval in accordance with measured R-R intervals in order to decrease the variability in the overall ventricular rhythm. The closer the length of the escape interval is to the intrinsic R-R interval, however, the greater the probability that a pace will be delivered coincident with an intrinsic beat. Even though ventricular pacing is inhibited by a ventricular sense occurring before expiration of the ventricular escape interval, a ventricular depolarization may begin some distance away from the sensing/pacing electrode in a different ventricle. The depolarization may then not be sensed in time to inhibit the pacing pulse because of the conduction delay before the depolarization wave reaches the sensing electrode. The result is a hemodynamically inefficient fusion beat which counteracts the otherwise beneficial effects of ventricular rate regularization in maintaining hemodynamic stability. In order to minimize this possibility, an intrinsic ventricular activation should be sensed as soon as possible in order to inhibit pacing. In typical heart failure patients with left bundle branch block, for example, the site of earliest ventricular activation is the right ventricle, and a right ventricular sensing channel is necessary to minimize the possibility of a fusion beat even when only the left ventricle is paced. The most flexible configuration is to use biventricular sensing channels so that the earliest activation occurring in either ventricle can be detected and used to inhibit pacing of one or both ventricles. In accordance with the present invention, therefore, ventricular regularization is implemented in a pacemaker having sensing channels for each ventricle so that a ventricular pace can be inhibited by a ventricular sense occurring in either ventricle.

When the system is configured for VRR with pacing of one ventricle only, a sensing refractory period can be initiated for the sensing channel of the non-paced ventricle by a ventricular pace. During this period, activity sensed by the channel are ignored for purposes of inhibiting and triggering pacing pulses. This sensing refractory period is of a duration sufficient to prevent detection of the depolarization resulting from the pacing pulse and conducted by cardiac tissue to the sensing electrode and can be programmable.

Figure 2:
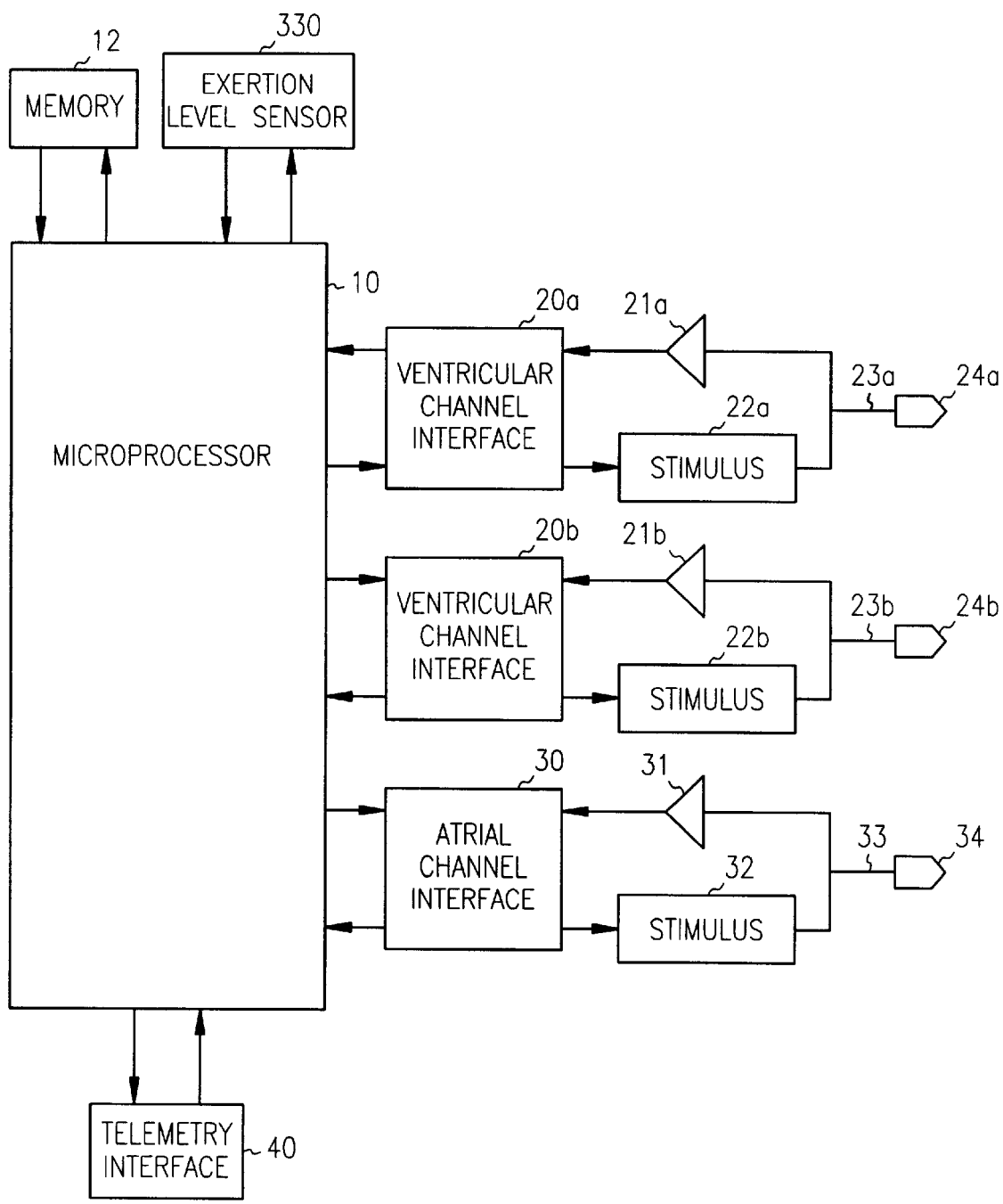
FIG. 2 is a system diagram of a microprocessor-based pacemaker.

FIG. 2 shows a system diagram of a pacemaker configured for biventricular sensing and pacing. (See, e.g., U.S. Pat. No. 4,928,688, issued to Mower and hereby incorporated by reference, for a description of biventricular pacing.) A microprocessor controller 10 communicates with a memory 12 via a bidirectional data bus, where the memory 12 typically comprises a ROM (read-only memory) for program storage and a RAM (random-access memory) for data storage. The controller is configured to control the operation of the pacemaker in accordance with a specified pacing mode as well as to implement the ventricular rate regularization mode described above. The pacemaker has atrial sensing and pacing channels comprising electrode 34, lead 33, sensing amplifier 31, pacing pulse generator 32, and an atrial channel interface 30 which communicates bidirectionally with a port of microprocessor 10. The device also has ventricular sensing and pacing channels for both ventricles comprising electrodes 24a–b, leads 23a–b, sensing amplifiers 21a–b, pacing pulse generators 22a–b, and ventricular channel interfaces 20a–b where "a" designates one ventricular channel and "b" designates the other. For each channel, the same lead and electrode are used for both sensing and pacing. The channel interfaces 20a–b and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. A telemetry interface 40 is also provided for communicating with an external programmer which allows a user to adjust parameter settings, change pacing modes, and receive data collected by the device. Also shown interfaced to the microprocessor 10 is an exertion level sensor 330 which may be, for example, an accelerometer or minute ventilation sensor. The exertion level sensor 330 is used to implement rate-adaptive pacing in which the LRL of the pacemaker is adjusted in accordance with exertion level measurements reflecting metabolic demand. Although the device shown in FIG. 2 is microprocessor-based, it should be understood that the logic and control functions to be described may equivalently be performed by any combination of discrete hardware components and/or software executed by the microprocessor.

The pacemaker depicted in FIG. 2 can be operated in either a biventricular or univentricular pacing mode. Other pacemakers suitable for practicing the present invention may have biventricular sensing channels but a pacing channel for only one ventricle. In any case, in order to lessen the probability of pacing a ventricle coincident with an intrinsic beat, a ventricular escape interval should be terminated by a ventricular sense from either ventricular sensing channel. The sensing channel for each ventricle thus allows operation in a ventricular rate regularization mode, where the ventricular escape interval is adjusted to be close to the intrinsic R-R interval, with less risk of producing fusion beats.

As described above, the R-R interval can be defined as the time between a present ventricular sense and the preceding ventricular sense or ventricular pace, with the instantaneous rate being the reciprocal of the measured interval. With biventricular sensing, either ventricular sensing channel can be used for defining the R-R intervals, but the first detected sense in a cardiac cycle is preferably used. As an approximation to using the first sense, advantage can be taken of the predominance of left bundle branch blocks in the CHF patient population. In these patients, the right ventricle depolarizes before the left ventricle, and using a right ventricular sense to define the R-R interval is a reasonable approximation for the first ventricular sense. This approximation simplifies the VRR and pacing algorithms when right ventricular senses are used to both define R-R intervals for VRR implementation and to define the cardiac cycle for bradycardia and tachycardia pacing.

In alternate embodiments of the invention, the R-R interval can be more particularly defined, depending upon whether a uni-ventricular or biventricular pacing mode is being used. In a uni-ventricular pacing mode, the R-R interval can be defined as the time from either a first ventricular sense or pace in the previous cardiac cycle to the first ventricular sense in the current cycle. In a biventricular pacing mode, the R-R interval can be defined as the time from a first ventricular sense of the previous cycle to the first ventricular sense of the current cycle, and as the time from a ventricular pace in the previous cycle to the first ventricular sense in the current cycle where the paced chamber of the previous cycle is the same chamber as the first ventricular sense of the current cycle.

The VRR algorithm adjusts the ventricular escape interval in accordance with measurements of R-R intervals. In univentricular pacing with biventricular sensing, the ventricular escape interval can be defined as the time between a first ventricular sense or pace and a subsequent pace if no intrinsic activity is detected. The ventricular escape interval may be more particularly defined for biventricular pacing modes as the time from the first ventricular sense of the previous cycle to a ventricular pace in the current cycle where the paced chamber of the current cycle is the same chamber as the first ventricular sense of the previous cycle, and as the time from a ventricular pace in the previous cycle to a ventricular pace in the same chamber during the current cycle.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac pacemaker, comprising:
    sensing right and left ventricular depolarizations through separate ventricular sensing channels and generating ventricular sense signals in accordance therewith;
    pacing a ventricle upon expiration of a ventricular escape interval without receiving a ventricular sense from either ventricular sensing channel, wherein the ventricular escape interval starts with either a ventricular pace or a ventricular sense, the reciprocal of the ventricular escape interval being the lower rate limit of the pacemaker;
    measuring an R-R interval associated with each ventricular sense, wherein an R-R interval is the time between a ventricular sense and the preceding ventricular sense or ventricular pace, the reciprocal of the R-R interval thus being the measured intrinsic ventricular rate; and,
    adjusting the ventricular escape interval in accordance with a measured R-R interval so that the lower rate limit adjusts in accordance with changes in the measured intrinsic ventricular rate.

2. The method of claim 1 wherein the ventricular escape interval is adjusted to move toward the measured R-R interval multiplied by a scaling factor.

3. The method of claim 2 wherein the ventricular escape interval is adjusted by computing a weighted average of the measured R-R interval multiplied by a scaling factor and the value of the ventricular escape interval.

4. The method of claim 1 wherein the ventricular escape interval is adjusted in accordance with a measured R-R interval after each ventricular sense.

5. The method of claim 1 further comprising adjusting the ventricular escape interval toward a value corresponding to a base lower rate limit after a ventricular pace.

6. The method of claim 5 wherein the ventricular escape interval is adjusted after a ventricular pace by multiplying the escape interval by a decay coefficient.

7. The method of claim 1 wherein the ventricular escape interval is adjusted by computing a weighted average of the measured R-R interval multiplied by a scaling factor and the previous value of the ventricular escape interval after each ventricular sense, and wherein the ventricular escape interval is adjusted by multiplying the escape interval by a decay coefficient after a ventricular pace.

8. The method of claim 7 wherein the scaling factor is selected to be greater than one such that the lower rate limit of the pacemaker is moved toward a fraction of the intrinsic ventricular rate after each ventricular sense.

9. The method of claim 7 wherein the scaling factor is selected to be less than one such that the lower rate limit of the pacemaker is moved toward a value that is above the intrinsic ventricular rate after each ventricular sense.

10. The method of claim 1 further comprising pacing a second ventricle upon expiration of the ventricular escape interval without receiving a ventricular sense from either ventricular sensing channel.

11. The method of claim 1 further comprising initiating a sensing refractory period for a non-paced ventricle after a ventricular pace during which time activity sensed in the non-paced ventricle is ignored.

12. The method of claim 1 wherein the R-R interval is defined as the time from a pace or first ventricular sense in the previous cardiac cycle to the first ventricular sense in the current cardiac cycle.

13. The method of claim 1 wherein the ventricular escape interval is defined as the time from a pace or first ventricular sense of the previous cardiac cycle to a ventricular pace in the current cardiac cycle.

14. The method of claim 10 wherein the R-R interval is defined as the time from a first ventricular sense of the previous cardiac cycle to the first ventricular sense of the current cycle, and as the time from a ventricular pace in the previous cardiac cycle to the first ventricular sense in the current cycle where the paced chamber of the previous cycle is the same chamber as the first ventricular sense of the current cycle.

15. The method of claim 10 wherein the ventricular escape interval is defined as the time from the first ventricular sense of the previous cycle to a ventricular pace in the current cycle where the paced chamber of the current cycle is the same chamber as the first ventricular sense of the previous cycle, and as the time from a ventricular pace in the previous cycle to a ventricular pace in the same chamber during the current cycle.

16. The method of claim 1 wherein the R-R interval is defined with respect to right ventricular senses.

17. A cardiac pacemaker, comprising:
    ventricular sensing channels for sensing right and left ventricular depolarizations and generating ventricular sense signals in accordance therewith;
    a ventricular pacing channel for pacing a ventricle;
    a controller for controlling operation of the pacemaker such that a ventricular pace is delivered upon expiration of a ventricular escape interval without receiving a ventricular sense from either ventricular sensing channel, wherein the ventricular escape interval starts with either a ventricular pace or a ventricular sense, the reciprocal of the ventricular escape interval being the lower rate limit of the pacemaker;
    wherein the controller is configured to measure an R-R interval associated with each ventricular sense, wherein an R-R interval is the time between a ventricular sense and the preceding ventricular sense or ventricular pace, the reciprocal of the R-R interval thus being the measured intrinsic ventricular rate; and, wherein the controller is configured to adjust the ventricular escape interval in accordance with a measured R-R interval so that the lower rate limit adjusts in accordance with changes in the measured intrinsic ventricular rate.

18. The pacemaker of claim 17 wherein the ventricular escape interval is adjusted to move toward the measured R-R interval multiplied by a scaling factor.

19. The pacemaker of claim 18 wherein the ventricular escape interval is adjusted by computing a weighted average of the measured R-R interval multiplied by a scaling factor and the previous value of the ventricular escape interval.

20. The pacemaker of claim 17 wherein the ventricular escape interval is adjusted in accordance with a measured R-R interval after each ventricular sense.

21. The pacemaker of claim 17 wherein the controller is configured to adjust the ventricular escape interval toward a value corresponding to a base lower rate limit after a ventricular pace.

22. The pacemaker of claim 21 wherein the controller is configured to adjust the ventricular escape interval after a ventricular pace by multiplying the escape interval by a decay coefficient.

23. The pacemaker of claim 17 wherein the controller is configured to adjust the ventricular escape interval by computing a weighted average of the measured R-R interval multiplied by a scaling factor and the previous value of the ventricular escape interval after each ventricular sense, and wherein the ventricular escape interval is adjusted by multiplying the escape interval by a decay coefficient after a ventricular pace.

24. The pacemaker of claim 23 wherein the scaling factor is selected to be greater than one such that the lower rate limit of the pacemaker is moved toward a fraction of the intrinsic ventricular rate after each ventricular sense.

25. The pacemaker of claim 24 wherein the scaling factor is selected to be less than one such that the lower rate limit of the pacemaker is moved toward a value that is above the intrinsic ventricular rate after each ventricular sense.

26. The pacemaker of claim 17 further comprising a second ventricular pacing channel for pacing a second ventricle.

* * * * *

UNITED STATES PATENT AND TRADEMARK OFFICE
CERTIFICATE OF CORRECTION

PATENT NO.      : 6,501,988 B2
DATED           : December 31, 2002
INVENTOR(S)     : Jian Ding et al.

It is certified that error appears in the above-identified patent and that said Letters Patent is hereby corrected as shown below:

<u>Title page,</u>
Item [56], U.S. PATENT DOCUMENTS, insert -- PG -- after "128/419".
Item [74], *Attorney, Agent, or Firm*, insert -- , -- after "Kluth".

Signed and Sealed this

Sixteenth Day of December, 2003

JAMES E. ROGAN
*Director of the United States Patent and Trademark Office*